United States Patent [19]
Yoon

[11] Patent Number: 5,540,648
[45] Date of Patent: Jul. 30, 1996

[54] MEDICAL INSTRUMENT STABILIZER WITH ANCHORING SYSTEM AND METHODS

[76] Inventor: InBae Yoon, 2101 Highland Ridge Dr., Phoenix, Md. 21131

[21] Appl. No.: 274,401

[22] Filed: Jul. 13, 1994

Related U.S. Application Data

[63] Continuation-in-part of Ser. No. 930,929, Aug. 17, 1992, Pat. No. 5,375,588, and Ser. No. 243,493, May 16, 1994.

[51] Int. Cl.$^6$ .................... A61B 1/00; A61B 1/01
[52] U.S. Cl. ............... 600/114; 600/102; 600/227; 606/1; 604/175
[58] Field of Search .................... 128/4, 20, 898; 602/6; 606/1, 108, 185; 604/174, 175; 600/114, 208, 227, 231, 233, 235, 102

[56] References Cited

U.S. PATENT DOCUMENTS

| | | |
|---|---|---|
| 667,768 | 2/1901 | DePuy . |
| 1,213,001 | 1/1917 | Philips . |
| 2,670,735 | 3/1954 | Brody ................ 128/214 |
| 2,898,917 | 8/1959 | Wallace . |
| 3,017,887 | 1/1962 | Heyer . |
| 3,039,468 | 6/1962 | Price . |
| 3,253,594 | 5/1966 | Matthews et al. . |
| 3,288,137 | 11/1966 | Lund . |
| 3,459,175 | 8/1969 | Miller . |
| 3,613,684 | 10/1971 | Sheridan . |
| 3,817,251 | 6/1974 | Hasson . |
| 3,856,020 | 12/1974 | Kovac . |
| 3,952,742 | 4/1976 | Taylor . |
| 4,077,412 | 3/1978 | Mossun . |
| 4,083,369 | 4/1978 | Sinnreich . |
| 4,161,175 | 7/1979 | Bentele . |
| 4,164,943 | 8/1979 | Hill et al. ............ 128/348 |
| 4,213,452 | 7/1980 | Shippert . |
| 4,327,716 | 5/1982 | Ansted . |
| 4,555,242 | 11/1985 | Saudager . |
| 4,593,681 | 6/1986 | Soni . |
| 4,608,965 | 9/1986 | Anspach, Jr. et al. . |
| 4,633,869 | 1/1987 | Schmieding . |
| 4,655,752 | 4/1987 | Honkanen et al. . |
| 4,666,433 | 5/1987 | Parks . |
| 4,670,008 | 6/1987 | Von Albertini . |
| 4,748,982 | 6/1988 | Horzewski et al. . |
| 4,944,732 | 7/1990 | Russo . |
| 4,957,124 | 9/1990 | Mooney . |
| 4,959,055 | 9/1990 | Hillyer . |
| 4,985,033 | 1/1991 | Boebel et al. . |
| 5,002,557 | 3/1991 | Hasson . |
| 5,009,643 | 4/1991 | Reich et al. . |
| 5,073,169 | 12/1991 | Raiken . |
| 5,112,321 | 5/1992 | Hiltebrandt . |
| 5,112,347 | 5/1992 | Taheri . |

(List continued on next page.)

FOREIGN PATENT DOCUMENTS

| | | |
|---|---|---|
| 0432363 | 6/1991 | European Pat. Off. . |
| 1184139 | 7/1959 | France . |
| 2653424 | 6/1978 | Germany . |
| 1113896 | 5/1968 | United Kingdom . |

*Primary Examiner*—Richard J. Apley
*Assistant Examiner*—Beverly M. Flanagan

[57] ABSTRACT

A medical instrument stabilizer for use in endoscopic procedures includes a stabilizer body for being placed against an external surface of an anatomical cavity wall and having a port for receiving medical instruments to be introduced into the anatomical cavity through the stabilizer body and the anatomical cavity wall. An anchoring system carried by the stabilizer body includes a tissue penetrating member movable between a retracted position wherein a tissue penetrating tip of the tissue penetrating member is disposed in a safe, non-exposed position and an extended position wherein the tissue penetrating tip extends from the stabilizer body to penetrate the anatomical wall and anchor the stabilizer thereon. Medical instruments inserted into the anatomical cavity through the port of the stabilizer are secured relative to the stabilizer and, therefore, the anatomical wall. Anchoring of the stabilizer to the anatomical wall by the tissue penetrating member permits manipulation of the anatomical wall by urging the stabilizer and/or the inserted instruments in a desired direction.

21 Claims, 5 Drawing Sheets

U.S. PATENT DOCUMENTS

| | | |
|---|---|---|
| 5,122,122 | 6/1992 | Allgood . |
| 5,137,520 | 8/1992 | Maxson et al. . |
| 5,147,316 | 9/1992 | Castillenti . |
| 5,176,669 | 1/1993 | Hasson et al. . |
| 5,176,697 | 1/1993 | Holmes et al. . |
| 5,183,033 | 2/1993 | Wilk . |
| 5,201,742 | 4/1993 | Hasson . |
| 5,215,531 | 6/1993 | Maxson et al. . |
| 5,217,441 | 6/1993 | Shichman . |
| 5,217,451 | 6/1993 | Freitas . |
| 5,222,508 | 6/1993 | Contarini . |
| 5,226,890 | 7/1993 | Ianniruberto et al. . |
| 5,232,451 | 8/1993 | Freitas et al. . |
| 5,234,455 | 8/1993 | Mulhollan . |
| 5,248,298 | 9/1993 | Bedi et al. . |
| 5,257,973 | 11/1993 | Villasuso ............... 604/175 X |
| 5,257,975 | 11/1993 | Foshee . |
| 5,258,003 | 11/1993 | Ciaglia et al. . |
| 5,263,939 | 11/1993 | Wortrich . |
| 5,267,968 | 12/1993 | Russo . |
| 5,267,969 | 12/1993 | Hirsch et al. . |
| 5,267,970 | 12/1993 | Chin et al. . |
| 5,271,380 | 12/1993 | Riek et al. . |
| 5,273,545 | 12/1993 | Hunt et al. . |
| 5,279,564 | 1/1994 | Taylor . |
| 5,279,575 | 1/1994 | Sugarbaker . |
| 5,284,130 | 2/1994 | Ratliff . |
| 5,284,474 | 2/1994 | Adair . |
| 5,290,249 | 3/1994 | Foster et al. . |
| 5,391,156 | 2/1995 | Hildwein et al. ............... 606/1 X |

MEDICAL INSTRUMENT STABILIZER WITH ANCHORING SYSTEM AND METHODS

CROSS-REFERENCE TO RELATED PATENT APPLICATIONS

This application is a continuation-in-part of patent applications Ser. No. 07/930,929, filed Aug. 17, 1992, now U.S. Pat. No. 5,357,588, and Ser. No. 243,493, filed May 16, 1994. The foregoing patent applications are incorporated herein by reference.

BACKGROUND OF THE INVENTION

1. Field of the Invention

The present invention pertains to medical instrument stabilizers particularly useful in endoscopic procedures for stabilizing medical instruments passing through an anatomical wall and, more particularly, to medical instrument stabilizers having anchoring systems for anchoring the stabilizers relative to the anatomical walls and to methods therefor.

2. Discussion of the Prior Art

Penetrating instruments including an outer sleeve or cannula and an obturator or penetrating member disposed within the outer sleeve or cannula have become extremely popular for use in surgical procedures to gain access to anatomical cavities, such as the abdomen. Such instruments are used to establish endoscopic portals for many various procedures, most notably laprascopic procedures, with access to the anatomical cavity being established via the outer or portal sleeve positioned to extend or pass through a wall of the cavity upon penetration into the cavity with the penetrating member. Once the portal sleeve extends through the thickness of the cavity wall, it is desirable to stabilize or secure the portal sleeve relative to the cavity wall to prevent withdrawal or backing out of the portal sleeve from the cavity, movement of the portal sleeve too far into the cavity as well as other movements of the portal sleeve which may be undesirable depending on the medical procedure being performed. Additionally, it is desirable in many various procedures to position the portal sleeve at an angle with the anatomical wall and to hold the portal sleeve in the angular position to optimize access to tissue and organ structures within the cavity.

Sufficient space for visualization and maneuvering within the cavity is typically achieved via insufflation of the cavity, such as to form a pneumoperitoneum. There are many disadvantages associated therewith, however, such as compressing the diaphragm and respiratory tract and collapsing the lungs.

SUMMARY OF THE INVENTION

Accordingly, it is a primary object of the present invention to overcome the disadvantages of prior art medical instrument stabilizers and methods therefor.

Another object of the present invention is to anchor a medical instrument stabilizer on an external surface of an anatomical wall with the use of one or more tissue penetrating members carried by the stabilizer.

A further object of the present invention is to penetrate an anatomical wall with a needle carried by a medical instrument stabilizer to anchor the stabilizer on an external surface of the anatomical wall to permit lifting or manipulation of the anatomical wall via the stabilizer or a medical instrument passing through a port of the stabilizer.

An additional object of the present invention is to arrange tissue penetrating members on a medical instrument stabilizer to allow the stabilizer to be anchored on an external surface of an anatomical wall such that a medical instrument passing through a port of the stabilizer is stabilized relative to the anatomical wall.

Yet another object of the present invention is to provide a medical instrument stabilizer having one or more tissue penetrating members movable between a retracted position wherein the tissue penetrating members are not exposed and an extended position wherein the tissue penetrating members protrude beyond a tissue engaging surface of the stabilizer and into the tissue to anchor the stabilizer to the tissue and to permit removal of the stabilizer from the tissue.

Some of the advantages of the present invention are that secure anchoring of a medical instrument stabilizer on an external surface of an anatomical wall is achieved with tissue penetrating members while permitting the medical instrument stabilizer to be handled with the tissue penetrating members in a safe, protected, non-exposed or retracted position, the tissue penetrating members can be disposed at various locations and angular orientations to facilitate anchoring for various endoscopic procedures, anatomical walls can be manipulated or lifted to provide increased exposure and to facilitate endoscopic diagnostic and surgical procedures, hollow tissue penetrating members can be used to permit medicaments, such as anesthetic agents, to be administered to surrounding tissue, and the medical instrument stabilizer is designed to facilitate use in a simple, quick and efficient manner with minimal trauma to the patient.

These and other objects, benefits and advantages are achieved with the present invention as generally characterized in a medical instrument stabilizer for use in the performance of endoscopic procedures in an anatomical cavity in the body and including a stabilizer body having a tissue engaging surface for being placed against an external surface of an anatomical cavity wall and a port extending through the stabilizer body for receiving medical instruments to be introduced into the anatomical cavity through the stabilizer body and the anatomical cavity wall. An anchoring system is carried by the stabilizer and includes a tissue penetrating member having a tip or end for penetrating tissue of the anatomical wall. The tissue penetrating member is movable between a retracted position wherein the tissue penetrating tip is disposed in a safe, non-exposed or protected position and an extended position wherein the tissue penetrating tip extends from the tissue engaging surface of the stabilizer body to penetrate the anatomical wall and anchor the stabilizer body on the anatomical wall. Medical instruments inserted into the anatomical cavity through the port of the stabilizer body and the anatomical wall are stabilized relative to the anatomical wall by the stabilizer, and anchoring of the stabilizer to the anatomical wall permits manipulation of the anatomical wall by urging the stabilizer and/or the inserted instruments in the desired direction.

The present invention is further characterized in a method of stabilizing medical instruments in endoscopic operative procedures in an anatomical cavity comprising the steps of placing a stabilizer body on an external surface of a wall of an anatomical cavity, extending a tissue penetrating member from the stabilizer body to penetrate the anatomical wall to anchor the stabilizer body on the anatomical wall, inserting a medical instrument through a port of the stabilizer body and the anatomical wall to enter the anatomical cavity and securing the instrument to the stabilizer body.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

The medical instrument stabilizer of the present invention can be utilized to stabilize any type of medical instrument relative to an anatomical wall, such as a wall forming an anatomical cavity; and, accordingly, while the medical instrument stabilizer is described herein for use with a portal sleeve or cannula for use in endoscopic procedures, such as laparoscopy, the medical instrument stabilizer can be used to anchor various other medical instruments including catheters and other small and large diameter cylindrical and non-cylindrical members. The anchoring system of the present invention is carried by the medical instrument stabilizer such that deployment of one or more tissue penetrating members or needles to penetrate tissue of an anatomical wall anchors the stabilizer to the anatomical wall allowing one or more medical instruments to be introduced into the anatomical cavity through one or more ports of the stabilizer.

Figure 1:
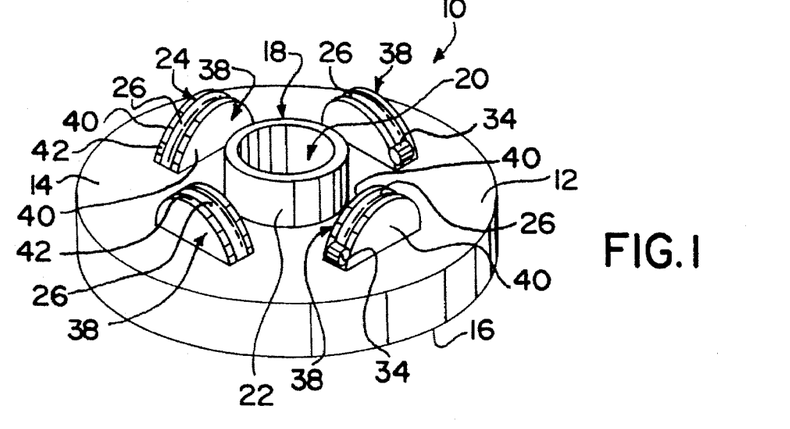
FIG. 1 is a perspective view of a medical instrument stabilizer having an anchoring system according to the present invention.

A medical instrument stabilizer 10 according to the present invention is illustrated in FIG. 1 and includes a body 12 of material, which can be a deformable, shape-retaining material or a non-deformable, non-shape-retaining material.

The stabilizer body 12 can be a layer, mat, plate, panel, sheet or piece of transparent, opaque or semi-opaque material having a desirable peripheral configuration and cross-section in accordance with procedural use. As shown in FIG. 1, the body 12 is disk-like and has a circular peripheral configuration with a uniform thickness defined between an upper surface 14 and a lower, tissue contacting or tissue engaging surface 16 of body 12. The material forming body 12 can include magnetic particles such that the body 12 can be used to magnetically attract and hold medical instruments in place. The body 12 can be formed as a solid member, or as a mesh with openings or interstices allowing air flow therethrough. Where the body 12 is made of a deformable, shape-retaining material, the material can be selected to permit the body 12 to be manually bent or otherwise shaped to form various configurations and can be constructed with sufficient strength and rigidity to retain the deformed configurations as disclosed in patent application Ser. No. 07/930,929, filed Aug. 17, 1992, and incorporated herein by reference.

Figure 2:
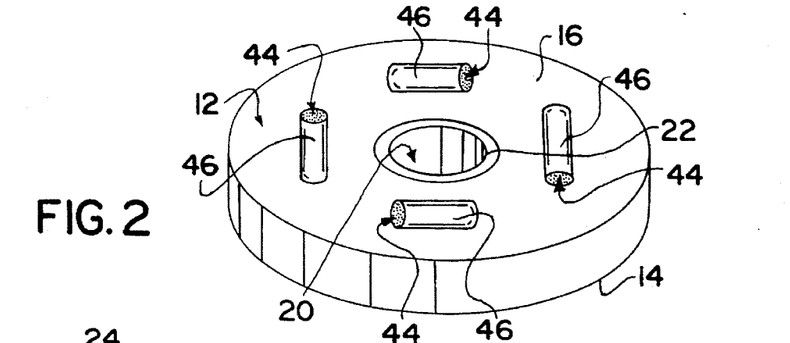
FIG. 2 is a bottom view of the medical instrument stabilizer of FIG. 1.

Body 12 includes one or more ports 18 defining a passage 20 therethrough for receiving medical instruments, one port 18 being shown for the stabilizer 10 of FIG. 1. Port 18 includes a passage 20 extending through the thickness of body 12 and can include additional structure, such as a tubular extension 22 having a lumen forming a continuation of passage 20. As shown in FIG. 1, tubular extension 22 extends upwardly from the upper surface 14 of body 12 to provide support for medical instruments inserted through passage 20 and/or to mount structure for locking or securing the inserted instruments as disclosed in the above-referenced patent application Ser. No. 07/930,929. The bottom of tubular extension 22 can terminate at the upper surface 14 or the tubular extension 22 can extend part way or entirely through body 12 to terminate within the body 12 or at the lower surface 16 thereof. As shown in FIG. 2, tubular extension 22 extends entirely through body 12 to terminate at lower surface 16. The tubular extension 22 can be formed integrally, unitarily with body 12 or the tubular extension 22 can be a separate member assembled to the body 12. The tubular extension 22 can be made of any suitable material, such as rubber or plastic; and, as shown for stabilizer 10, the tubular extension 22 is made from resilient, stretchable material allowing medical instruments of various sizes to be inserted in passage 20 with the resilient material of the tubular extension gripping the medical instruments. Passage 20 can be sized to frictionally grip a medical instrument inserted therethrough to prevent backing out of the instrument and/or to form a seal therewith or separate locking structure can be provided to lock or secure the instruments in place. Ports 18 can include various joint members or angularly orienting portions for selectively changing the angular orientation of passage 20 allowing the angular orientation of medical instruments inserted therethrough to be selectively adjusted as disclosed in prior application Ser. No. 07/930,929.

An anchoring system 24 is carried by the stabilizer 10 and includes one or more tissue penetrating members, such as anchoring needles 26, extendable from stabilizer body 12. Needles 26 are movably mounted on or in body 12 or by structure mounted on body 12 to be movable between a safe, protected, non-exposed or retracted position to an extended position wherein needles 26 protrude from the lower surface 16 of body 12. As shown in FIG. 1, four needles 26 are provided for the stabilizer 10; however, the number of needles 26 can vary in accordance with the size and configuration of body 12 as necessary to secure the body 12 on an external surface of an anatomical wall as described further below.

Figure 3:
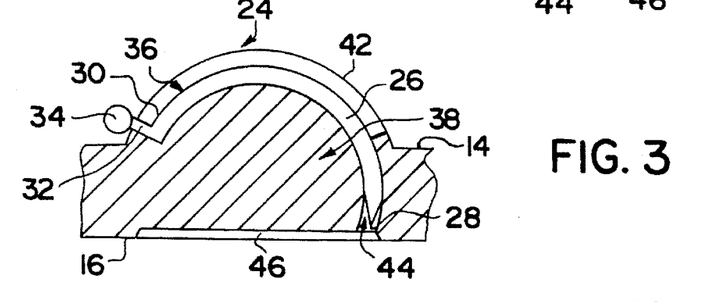
FIG. 3 is an enlarged, fragmentary sectional view of the medical instrument stabilizer of FIG. 1 with the anchoring system in a retracted position.
Figure 4:
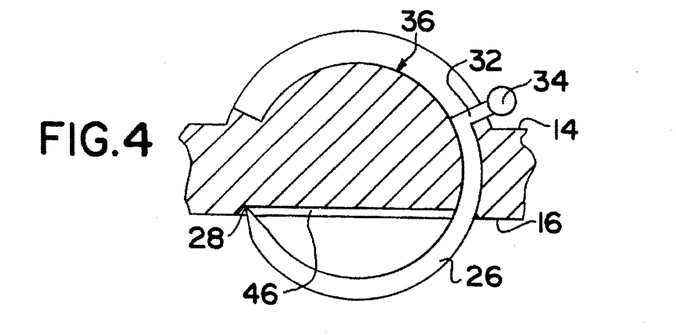
FIG. 4 is an enlarged, fragmentary sectional view of the medical instrument stabilizer of FIG. 1 with the anchoring system in an extended position.

As shown in FIGS. 3 and 4, each needle 26 includes an arcuate or semi-circular body of circular cross-section having a distal end 28 terminating at a sharp tip for penetrating anatomical tissue and a proximal end 30 connected with an arm or pin 32 extending radially outwardly from needle 26 to terminate at a knob 34. Needles 26 are normally disposed in tracks, grooves, channels, pockets or cavities 36 formed within or on body 12 to be in the protected, non-extended or retracted position. Channels 36 are formed in arcuate or semi-circular flanges 38 disposed on the upper surface 14 of body 12. Flanges 38, one of which is provided for each needle 26, can have various configurations to mount needles 26 in the safe, retracted position and to provide a track or guide for extension of needles 26 from body 12. As shown in FIG. 1, each flange 38 extends perpendicularly from upper surface 14 and includes parallel or substantially parallel planar side walls 40 joined by an arcuate or curved upper wall 42. Upper walls 42 have a radius of curvature corresponding to the radius of curvature of needles 26, and the channels 36 extend along the upper walls 42 within the thickness of body 12 to follow the radius of curvature of the needles 26. As shown in FIGS. 3 and 4, channels 36 extend downwardly through body 12 to terminate at openings 44 along lower surface 16. As shown in FIG. 2, openings 44 are disposed in recesses 46 along lower surface 16 aligned with needles 26. The length of recesses 46 is selected such that the distal ends 28 of the needles 26 will be received in the recesses 46 when the needles 26 are in a fully extended position as shown in FIG. 4 and as described further below.

Needles 26 are disposed in channels 36 with arms 32 protruding from channels 36 such that knobs 34 are disposed in a position to be easily grasped by a surgeon during use. Needles 26 can be arranged on the stabilizer 10 in many various ways in accordance with the size and configuration of the body 12 and the procedure being performed. As shown in FIG. 1, the needles 26 are arranged on body 12 at 90° spaced locations. A first pair of needles 26 disposed 180° from one another are contained in first planes parallel to one another. A second pair of needles 26 disposed 180° from one another are contained in second planes parallel to one another and transverse to the first planes.

Figure 5:
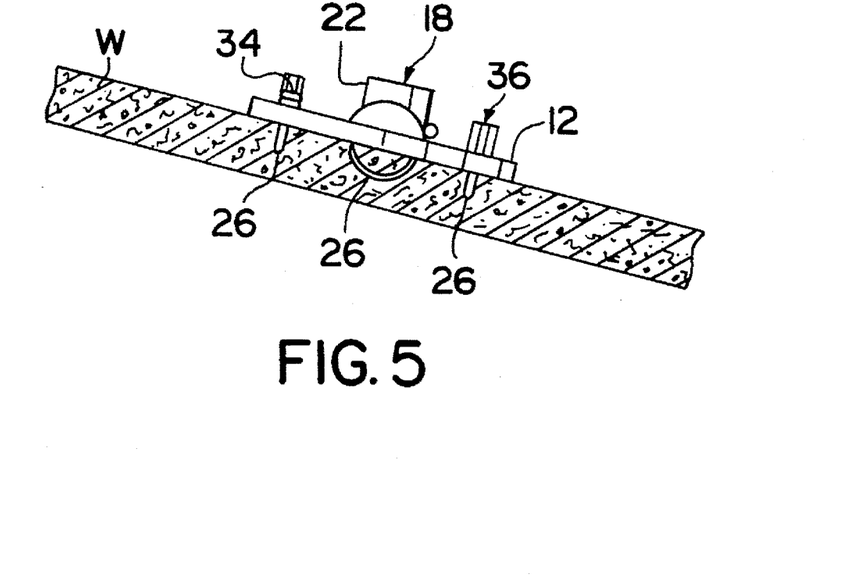
FIG. 5 is a broken view, partly in section, of the medical instrument stabilizer of FIG. 1 in use on an external surface of an anatomical wall.

The medical instrument stabilizer 10 is normally provided with needles 26 in the retracted position as shown in FIGS. 1 and 3 wherein the knobs 34 are disposed at first ends of channels 36 with the first ends of the channels 36 providing stops for knobs 34. In the retracted position, the distal ends 28 of needles 26 are disposed in channels 36 to be in a safe, non-exposed position. When it is desired to utilize the medical instrument stabilizer 10, the tissue engaging surface 16 is positioned on an external surface of an anatomical wall, such as a wall W of an anatomical cavity, such as the abdomen, with the port 18 positioned at a desired location for introduction of a portal sleeve or other instrument and with the tissue penetrating members 26 in the retracted position. The stabilizer body 12 is held against the external surface of the anatomical wall, and the knobs 34 are manually grasped and moved along the channels 36. Movement of knobs 34 along the channels 36, i.e. toward second ends of the channels 36, causes needles 26 to be extended from body 12 to penetrate into the tissue of the anatomical wall as shown in FIG. 5. During penetration, the distal end 28 of each needle 26 is displaced through the opening 44 to extend from the tissue engaging surface 16 and into the anatomical wall W. The needles 26 are extended to a desired extent to capture tissue between the arcuate body of each needle 26 and the body 12 of the stabilizer 10 thereby anchoring the stabilizer 10 in place. Since movement of knob 34 causes concomitant movement of needle 26, the position of each needle 26 within the anatomical wall W can be gauged by observing the position of the knobs 34. Various locking mechanisms can be provided in the stabilizer 10 to lock the needles 26 in various extended positions as disclosed in prior application Ser. No. 243,493 incorporated herein by reference.

Figure 6:
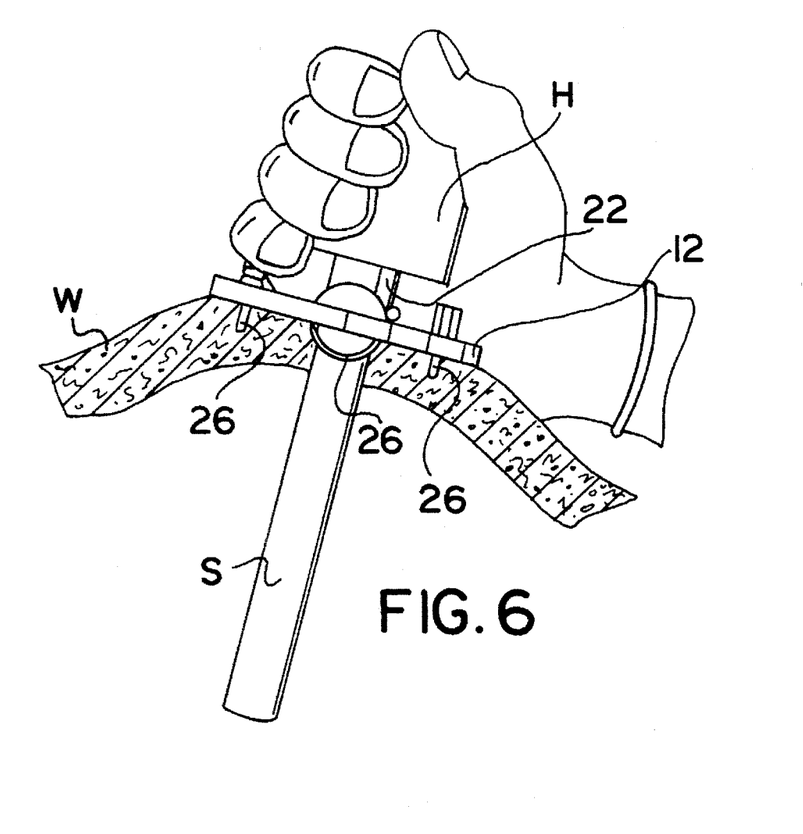
FIG. 6 is a broken view, partly in section, of the medical instrument stabilizer of FIG. 1 lifting the anatomical wall.

FIG. 4 illustrates needle 26 in a fully extended position at which time knob 34 is disposed at the second end of channel 36 and tip 28 of the needle 26 is received in recess 46 with the second end of channel 36 providing a stop for knob 34. Once the stabilizer 10 is secured in place by anchoring system 24, a medical instrument, such as a penetrating instrument including a penetrating member and a portal sleeve S, can be introduced through tubular extension 22 for penetration through the anatomical wall W and into the anatomical cavity. Tubular extension 22 grips the portal sleeve S; and, with the needles 26 penetrating into the anatomical wall W, the stabilizer 10 and anchoring system 24 of the present invention permits manipulation or lifting of the wall W of the anatomical cavity to improve exposure, for example, as well as anchors the stabilizer 10 to the cavity wall and, therefore, anchors portal sleeve S extending therethrough. Movement of the anatomical wall W is easily accomplished by grasping the stabilizer 10 and/or the inserted instrument and urging it in the desired direction. As shown in FIG. 6, the anatomical wall W is being manipulated by grasping and gently pulling on a housing H mounting the portal sleeve S. The needles 26 can be moved to the retracted position at any time to permit repositioning of medical instruments introduced through the stabilizer 10 and for removal of stabilizer 10 from the anatomical wall W.

Figure 7:
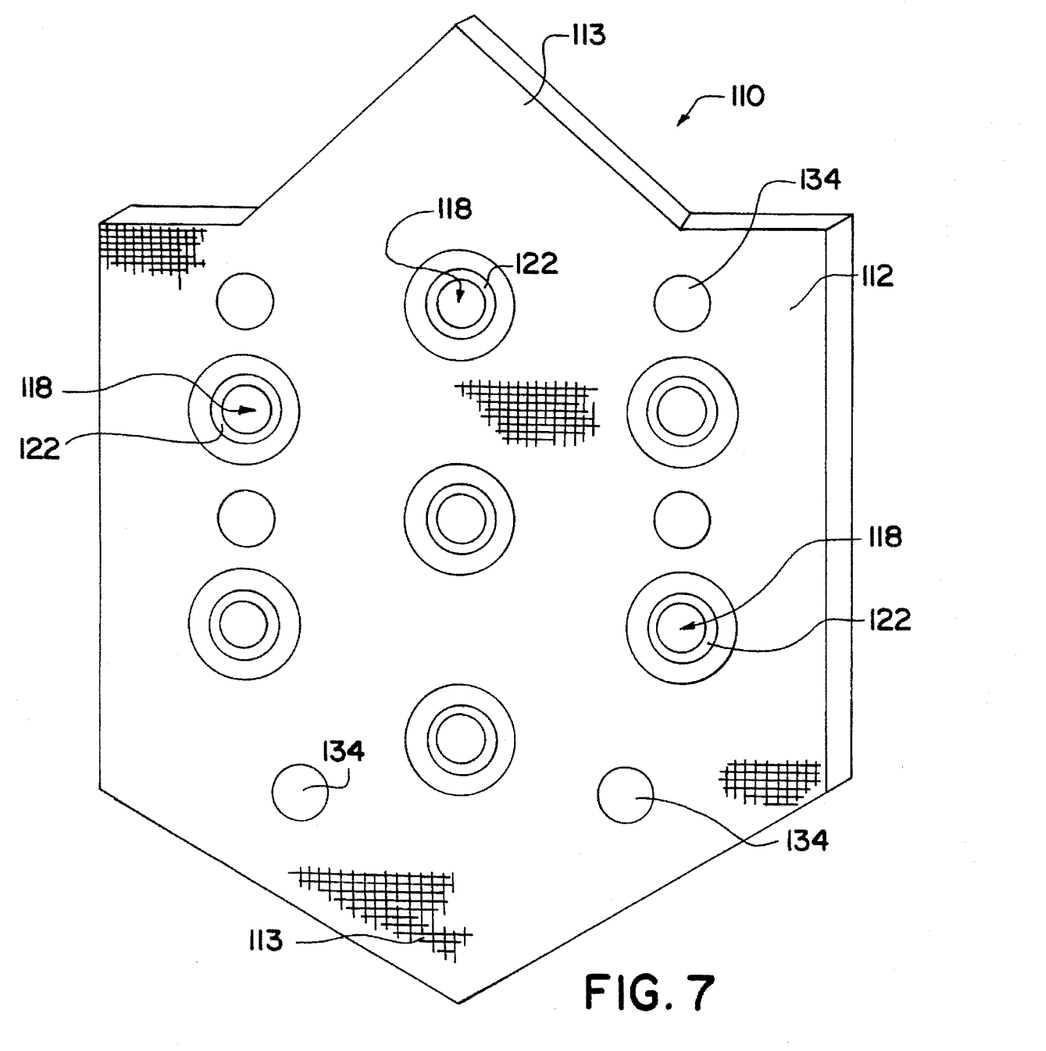
FIG. 7 is a perspective view of a modification of a medical instrument stabilizer according to the present invention.
Figure 8:
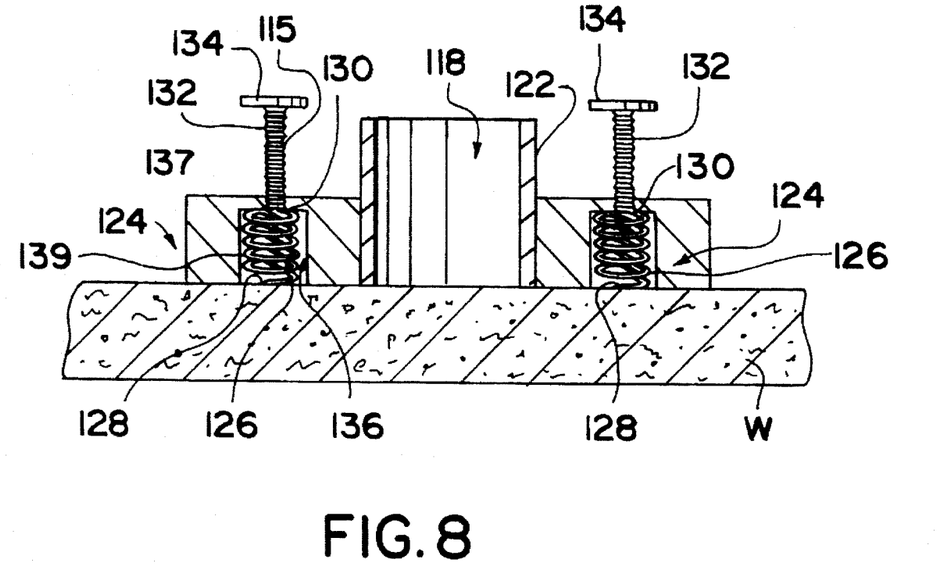
FIG. 8 is a broken view, partly in section, of the medical instrument stabilizer of FIG. 7 with the anchoring system in the retracted position.
Figure 9:
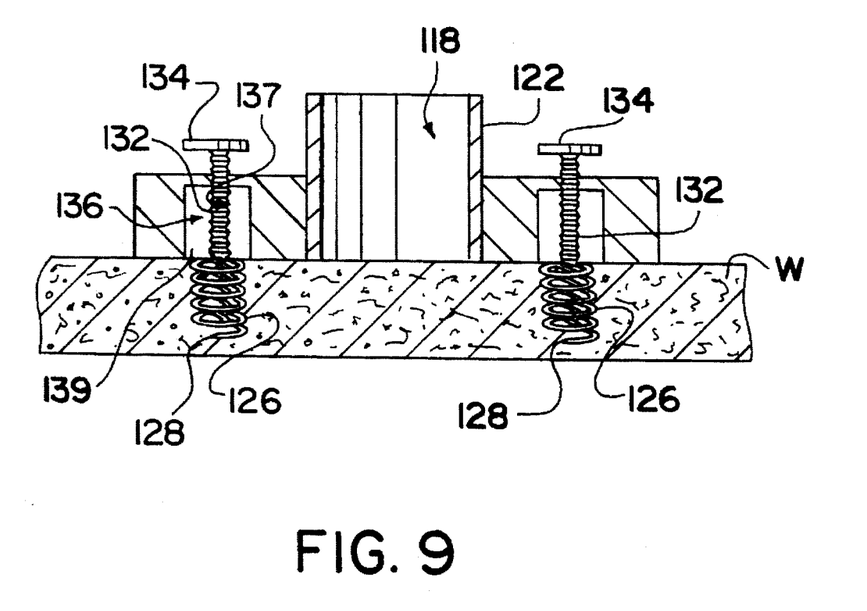
FIG. 9 is a broken view, partly in section, of the medical instrument stabilizer of FIG. 7 with the anchoring system in the extended position.

A modification of a stabilizer having an anchoring system according to the present invention is illustrated in FIG. 7 at 110. The stabilizer 110 includes a body 112 made of a deformable, shape-retaining material. Body 112 is generally square in peripheral configuration with tapered extensions 113 at opposing sides thereof for alignment with the xiphoid process when the stabilizer 110 is used on the abdomen. A plurality of ports 118 having tubular extensions 122 are arranged on body 12 at spaced locations to provide flexibility for the surgeon when introducing medical instruments through the stabilizer 10 and into anatomical cavities. As shown in FIGS. 8 and 9, anchoring system 124 for stabilizer 110 includes tissue penetrating members or needles 126 arranged on body 112 at various locations. Each needle 126 has a spiral or corkscrew configuration terminating at a distal end 128 for penetrating anatomical tissue and at a proximal end 130 connected with an arm 132 carrying a knob 134 disposed externally of body 112 for convenient grasping by a surgeon. Arms 132 extend through channels 136 formed through the thickness of body 112, the channels 136 having an upper portion 137 for guiding movement of arms 132 and a lower portion 139 for housing needles 126 in the retracted position. Arms 132 carry an external thread 115 for engagement with an internal thread along channel upper portion 137 for controlled deployment of needles 126 via rotation of knobs 134.

Use of medical instrument stabilizer 110 is similar to that previously described except that needles 126 are moved between the retracted and extended positions via rotation of knobs 134 to penetrate an anatomical wall W with a rotational penetrating motion. Once the stabilizer 110 has been positioned on the external surface of an anatomical wall W, knobs 134 are manually grasped and rotated causing the spiral needles 126 to be rotated into the tissue of the anatomical wall. Needles 126 can be extended a desired extent from body 112 as gauged by the position of knobs 134 with the threads preventing extension of needles 126 beyond that which is desired. With the needles 126 penetrating the anatomical wall W, the stabilizer 110 will be secured in place for stabilization of instruments introduced through ports 118 while allowing manipulation of the anatomical wall via the stabilizer 110 and/or the inserted instruments.

Figure 10:
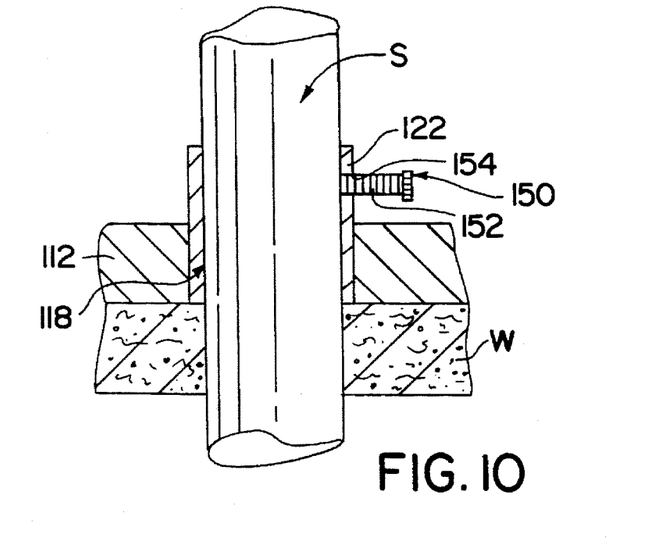
FIG. 10 is a broken view, partly in section, of the medical instrument stabilizer of FIG. 7 illustrating a locking member for securing a medical instrument in the port of the stabilizer.

FIG. 10 illustrates stabilizer 110 secured on anatomical wall W as previously described with a portal sleeve S passing through the stabilizer body 112 and the anatomical wall W to enter the anatomical cavity. As also shown in FIG. 10, a locking mechanism can be provided in the stabilizers of the present invention to secure instruments introduced through the ports of the stabilizers. The locking mechanism illustrated in FIG. 10 includes a locking member 150, which is in the nature of a screw having a shaft 152 with external threads thereon for cooperatively engaging internal threads of a passage 154 extending through the wall of tubular extension 122. Accordingly, rotation of locking member 150 causes advancement of the shaft 152 thereof into the lumen of tubular extension 122 such that the shaft 152 engages the portal sleeve S to lock the portal sleeve in port 118. It should be appreciated that the locking mechanism shown in FIG. 10 is provided by way of example and that various other locking mechanisms can be provided in the stabilizers of the present invention to secure inserted instruments in the ports of the stabilizers.

Figure 11:
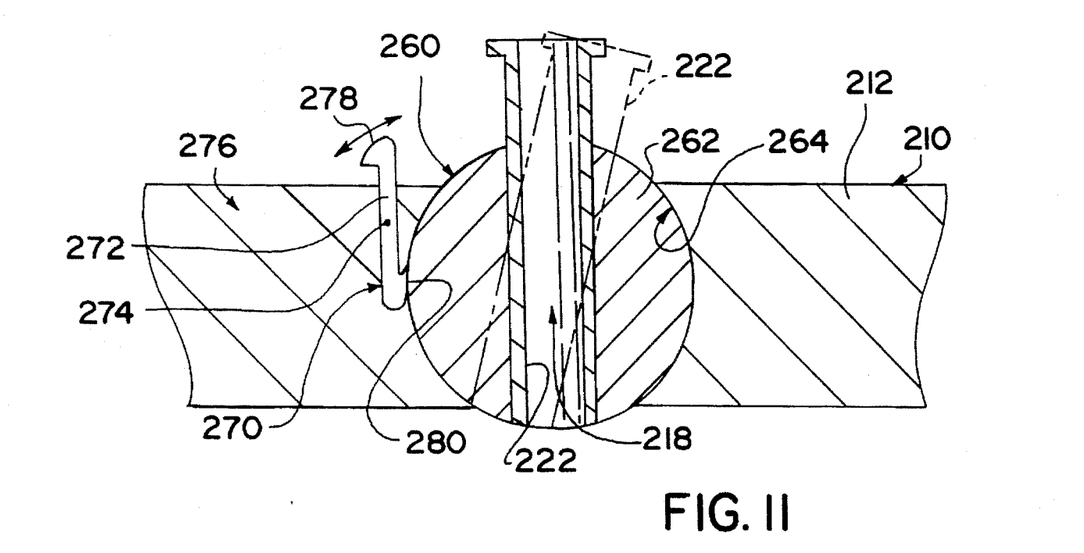
FIG. 11 is a broken view, partly in section, of another modification of a medical instrument stabilizer according to the present invention.

FIG. 11 illustrates at 210 a modification of a stabilizer according to the present invention wherein the stabilizer 210 includes one or more ports 218 having angularly orienting portions 260. Stabilizer 210 is similar to stabilizers 10 and 110 and includes a body 212 having one or more ports 118 and an anchoring system (not shown). Ports 118 include angularly orienting portions or joints 260, each of which includes a ball 262 rotatably mounted in recesses or sockets 264 in the thickness of body 212. Balls 262 have axial passages therethrough for receiving tubular extensions 222. Balls 262 can be formed of any suitable material, such as rubber or plastic, and can be mounted on body 212 in many various ways allowing extensions 222 to be angularly positioned relative to the body 212 as shown in broken lines in FIG. 11.

Once rotated to position extensions 222 at a desired angle, balls 262 can be locked in place with a locking mechanism 270. Locking mechanism 270 includes a locking bar 272 pivotally mounted on a pin 274 mounted to body 212 with the locking bar 272 being disposed in a slot 276 in body 212. Locking bar 272 extends upwardly through slot 276 to terminate at a knob 278 for being grasped by a surgeon. An end of the locking bar 272 disposed in slot 276 has a hook-like projection or finger 280 for being selectively lockingly engaged and disengaged with ball 262 in response to rotation of locking bar 272 about pin 274 as shown by the arrow in FIG. 11. It should be appreciated that the angularly orienting portion and locking mechanism therefor are illustrated herein by way of example, and that various other angularly orienting portions and locking mechanisms therefor can be utilized in the present invention. Various angularly orienting portions and locking mechanisms suitable for use in the present invention are disclosed in prior application Ser. No. 930,929 incorporated herein by reference.

The use of tissue penetrating members, such as needles, for anchoring a stabilizer upon an external surface of an anatomical wall is particularly advantageous since lifting or manipulation of the anatomical wall is facilitated by secure engagement of the stabilizer with the anatomical wall.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A medical instrument stabilizer for use in the performance of endoscopic procedures in an anatomical cavity in the body comprising:

a stabilizer body having a surface for being placed against an external surface of a wall of an anatomical cavity and a port for receiving instruments to be introduced into the anatomical cavity through said stabilizer body and the cavity wall; and a tissue penetrating member movably carried by said stabilizer body and having a tip extendable from said stabilizer surface and into the cavity wall for anchoring said stabilizer body on the cavity wall, said tissue penetrating member being movable between a retracted position wherein said tip is disposed within said body and an extended position wherein said tip extends from said stabilizer surface.

2. A medical instrument stabilizer as recited in claim 1 and further including a channel in said stabilizer body within in which said tip is disposed in said retracted position, said channel having an opening along said stabilizer surface for extension of said tip from said stabilizer surface.

3. A medical instrument stabilizer as recited in claim 2 and further including means coupled with said tissue penetrating member for moving said tissue penetrating member between said retracted position and said extended position.

4. A medical instrument stabilizer as recited in claim 3 wherein said means for moving includes means for selectively controlling extension of said tip from said stabilizer surface in said extended position.

5. A medical instrument stabilizer as recited in claim 4 wherein said means for moving includes a knob for manually moving said tissue penetrating member through said channel.

6. A medical instrument stabilizer as recited in claim 5 wherein said means for moving permits movement of said tissue penetrating member between said retracted position and a fully extended position and further including a recess along said stabilizer surface for receiving said tip when said tissue penetrating member is in said fully extended position.

7. A medical instrument stabilizer as recited in claim 1 wherein said stabilizer body is made of deformable, shape-retaining material.

8. A medical instrument stabilizer as recited in claim 1 wherein said tissue penetrating member includes a needle.

9. A medical instrument stabilizer as recited in claim 8 wherein said needle has an arcuate configuration.

10. A medical instrument stabilizer as recited in claim 8 wherein said needle has a spiral configuration.

11. A medical instrument stabilizer as recited in claim 1 wherein said stabilizer body has a thickness and said port extends through said thickness of said stabilizer body.

12. A medical instrument stabilizer as recited in claim 1 wherein said stabilizer body includes a plurality of ports.

13. A medical instrument stabilizer as recited in claim 1 wherein said port includes means for securing medical instruments inserted through said port relative to said stabilizer body.

14. A medical instrument stabilizer as recited in claim 1 wherein said stabilizer body carries a plurality of said tissue penetrating members.

15. A method of stabilizing a medical instrument in endoscopic operative procedures in an anatomical cavity comprising the steps of:

placing a stabilizer body on an external surface of a wall of the anatomical cavity;

extending a tissue penetrating member from the stabilizer body to penetrate the anatomical wall to anchor the stabilizer body on the anatomical wall, said step of extending including moving the tissue penetrating member from a retracted position within the body to an extended position extending from the lower surface;

inserting a medical instrument through a port of the stabilizer body and the anatomical wall to enter the anatomical cavity; and securing the medical instrument relative to the stabilizer body.

16. A method of stabilizing a medical instrument as recited in claim 15 wherein said step of placing includes placing a lower surface of the stabilizer body on the external surface of the anatomical wall.

17. A method of stabilizing a medical instrument as recited in claim 15 wherein said step of extending includes manually moving the tissue penetrating member.

18. A method of stabilizing a medical instrument as recited in claim 17 wherein said step of manually moving includes moving a knob coupled with the tissue penetrating member along a channel of the stabilizer body.

19. A method of stabilizing a medical instrument as recited in claim 17 wherein said step of manually moving includes rotating a knob coupled with the tissue penetrating member.

20. A method of stabilizing a medical instrument as recited in claim 15 wherein said step of extending includes controlling extension of the tissue penetrating member from the stabilizer body.

21. A method of stabilizing a medical instrument in endoscopic operative procedures in an anatomical cavity comprising the steps of:

placing a stabilizer body on an external surface of a wall of the anatomical cavity;

extending a tissue penetrating member from the stabilizer body to penetrate the anatomical wall to anchor the stabilizer body on the anatomical wall;

inserting a medical instrument through a port of the stabilizer body and the anatomical wall to enter the anatomical cavity;

securing the medical instrument relative to the stabilizer body; and manipulating the anatomical wall by moving the inserted medical instrument in a desired direction.

* * * * *